United States Patent [19]

Yamanaka et al.

[11] Patent Number: 5,058,442
[45] Date of Patent: Oct. 22, 1991

[54] APPARATUS FOR MEASURING LIQUID VAPOR ADSORPTION AND DESORPTION CHARACTERISTICS OF A SAMPLE

[75] Inventors: Shoji Yamanaka, Hiroshima, Japan; Sridhar Komarneni, Altoona, Pa.

[73] Assignee: Gas Research Institute, Chicago, Ill.

[21] Appl. No.: 310,640

[22] Filed: Feb. 15, 1989

[51] Int. Cl.$^5$ .............................................. G01N 15/08
[52] U.S. Cl. ........................................ 73/865.5; 73/38
[58] Field of Search ................................. 73/38, 865.5

[56] References Cited

U.S. PATENT DOCUMENTS

| | | | |
|---|---|---|---|
| 2,729,969 | 1/1956 | Innes | 73/38 |
| 3,059,478 | 10/1962 | Coggeshall et al. | 73/38 x |
| 3,211,006 | 10/1965 | Haley | 73/865.5 |
| 3,262,319 | 7/1966 | Orr et al. | 73/38 X |
| 3,295,720 | 1/1967 | Slone | 73/865.5 X |
| 3,349,625 | 10/1967 | Benusa | 73/865.5 |
| 3,464,273 | 9/1969 | Hendrix et al. | 73/865.5 |
| 3,555,912 | 1/1971 | Lowell | 73/38 X |
| 3,707,870 | 1/1973 | Herve et al. | 73/38 |
| 3,732,736 | 5/1973 | Glaude et al. | 73/865.5 |
| 3,771,367 | 11/1973 | Lowell et al. | 73/865.5 |
| 3,850,040 | 11/1974 | Orr et al. | 73/38 X |
| 4,305,291 | 12/1981 | Nelson | 73/865.5 |
| 4,489,593 | 12/1984 | Pieters et al. | 73/38 |
| 4,528,850 | 7/1985 | Witier | 73/865.5 |
| 4,566,326 | 1/1986 | Lowell | 73/38 X |
| 4,762,010 | 8/1988 | Borghard et al. | 73/865.5 |

FOREIGN PATENT DOCUMENTS 1057798 5/1959 Fed. Rep. of Germany.
1202540 10/1965 Fed. Rep. of Germany.

OTHER PUBLICATIONS

Vacuum 3 (3)254–278 (1953): Joy, *Methods and Techniques for the Determination of Specific Surface by Gas Absorption.*
Aminco Lab News, Spring 1966, p. 14.
Aminco Lab News, Winter 1967, pp. 9, 10.
*Encyclopedia of Chemistry*, 3rd ed. (1973): C. A. Hampel & G. G. Hawley, editors, pp. 22–25.
*Experiments in Physical Chemistry*, 3rd ed. (1974): D. P. Shoemaker et al pp. 64–380.

Primary Examiner—Hezron E. Williams
Assistant Examiner—Joseph W. Roskos
Attorney, Agent, or Firm—Oblon, Spivak, McClelland, Maier & Neustadt

[57] ABSTRACT

In order to measure the adsorption and desorption characteristics of water vapor by a porous or powdery sample, the sample is placed in an automated device which measures the difference between an equilibrium pressure and a sample pressure for various values of sample pressures, during both adsorption and desorption. A programmable computer calculates the amount of water vapor adsorption and desorption based upon the equilibrium pressure and can be used to control a printer for plotting the resulting data.

13 Claims, 10 Drawing Sheets

APPARATUS FOR MEASURING LIQUID VAPOR ADSORPTION AND DESORPTION CHARACTERISTICS OF A SAMPLE

BACKGROUND OF THE INVENTION

1. Field of the Invention:

The present invention relates to an apparatus for measuring the amount of liquid vapor which is adsorbed or desorbed by a sample at various pressures. More specifically, the invention relates to an apparatus for measuring water vapor adsorption and desorption characteristics of porous materials and fine powder materials with fine particle sizes.

2. Brief Description of the Related Art:

In the characterization of porous materials and powder materials with fine particle sizes, the measurement of nitrogen adsorption-desorption isotherms for various pressures at the liquid nitrogen temperature is known. The analysis of the isotherms gives useful information about the pore structure, pore size distribution, surface area and porosity of the materials. Although the analysis of nitrogen adsorption-desorption characteristics is satisfactory for the analysis of many materials, other materials such as zeolites, clays, xerogels, catalysts, cements and ceramic powders, which are used in air or in humid atmosphere require analysis by adsorption-desorption isotherms of water vapor as well as nitrogen.

SUMMARY OF THE INVENTION

It is accordingly an object of the invention to provide an apparatus for automatically measuring liquid vapor adsorption and desorption characteristics of a sample.

It is a further object of the invention to provide an apparatus for automatically measuring liquid vapor adsorption and desorption characteristics of a sample and producing water vapor adsorption and desorption isotherms for the sample.

In order to carry out the above, and other, objects, the invention includes an apparatus for measuring liquid vapor adsorption and desorption characteristics of a sample, the apparatus including a fluid tight sample holding volume, a sealed volume, pressure sensing means, first fluid tight conduit means for fluidically communicating the sample holding volume with the sealed volume and the pressure sensing means, a liquid holding volume, and an evacuatable volume, second fluid tight conduit means for fluidically communicating the fluid holding volume and the evacuatable volume, vacuum forming means, first automatically controllable valve means in the first conduit means and selectively actuatable for isolating the sample holding volume from the sealed volume and the pressure sensing means, second automatically controllable valve means selectively actuatable for fluidically communicating the first and second conduit means, means for selectively isolating either the liquid holding volume or the evacuatable volume from the second conduit means, third automatically controllable valve means selectively actuatable for fluidically communicating the vacuum forming means with the second conduit means, and control means. The control means include means for receiving pressure signals from the pressure sensing means, means for storing a program, and means responsive to the pressure signals for selectively controlling the first, second and third valve means in accordance with a program stored in the program storing means.

According to a further feature of the invention, the means for selectively controlling the valve means includes adsorption measuring means for simultaneously opening the first, second and third valve means whereby the sample holding volume and the sealed volume and the liquid holding volume and the evacuatable volume are evacuated, means for subsequently opening the second valve means while the evacuatable volume is isolated from the second conduit means whereby liquid vapor in the liquid holding volume is permitted to enter the sealed volume, means for closing the second valve means when a detected pressure $P_i$ in the sealed volume exceeds a predetermined fraction $P_n$ of a maximum tested vapor pressure $P_0$, means for subsequently opening the first valve means, whereby a sample in the sample holding volume is exposed to the pressure $P_i$ and liquid vapor is adsorbed on the sample, and means for closing the first valve means when an equilibrium pressure $P_e$ is detected in the sealed volume.

The control means also includes means for determining an amount $\Delta a$ of liquid vapor adsorbed by the sample, based upon a value of $P_i - P_e$.

According to a further feature of the invention, the control means further comprises means for testing whether $P_e$ is equal to or greater than $P_t$, and for storing values of $\Delta a$ when $P_e$ is approximately equal to $P_0$.

According to another feature of the invention, the control means includes means for testing whether $\Delta a$ is greater than a threshold value and increasing $P_n$ to a larger fraction of $P_0$ when $\Delta a$ is not greater than the threshold value and $P_e$ is less than $P_t$.

According to a further feature of the invention, the control means includes means for determining when an equilibrium pressure is detected in the sample holding means. The means for determining when an equilibrium pressure is detected in the sample holding means includes timer means for detecting the passage of a predetermined time, and means for outputting an equilibrium pressure signal when $P_i$ changes by less than a set value during the predetermined time.

According to a further feature of the invention, means for plotting values of $\Delta a$ at different values of $P_n$ are provided.

Desorption measuring means corresponding to the adsorption measuring means are also provided

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENT

A preferred embodiment of the invention will now be described with reference to the attached figures.

Figure 1:
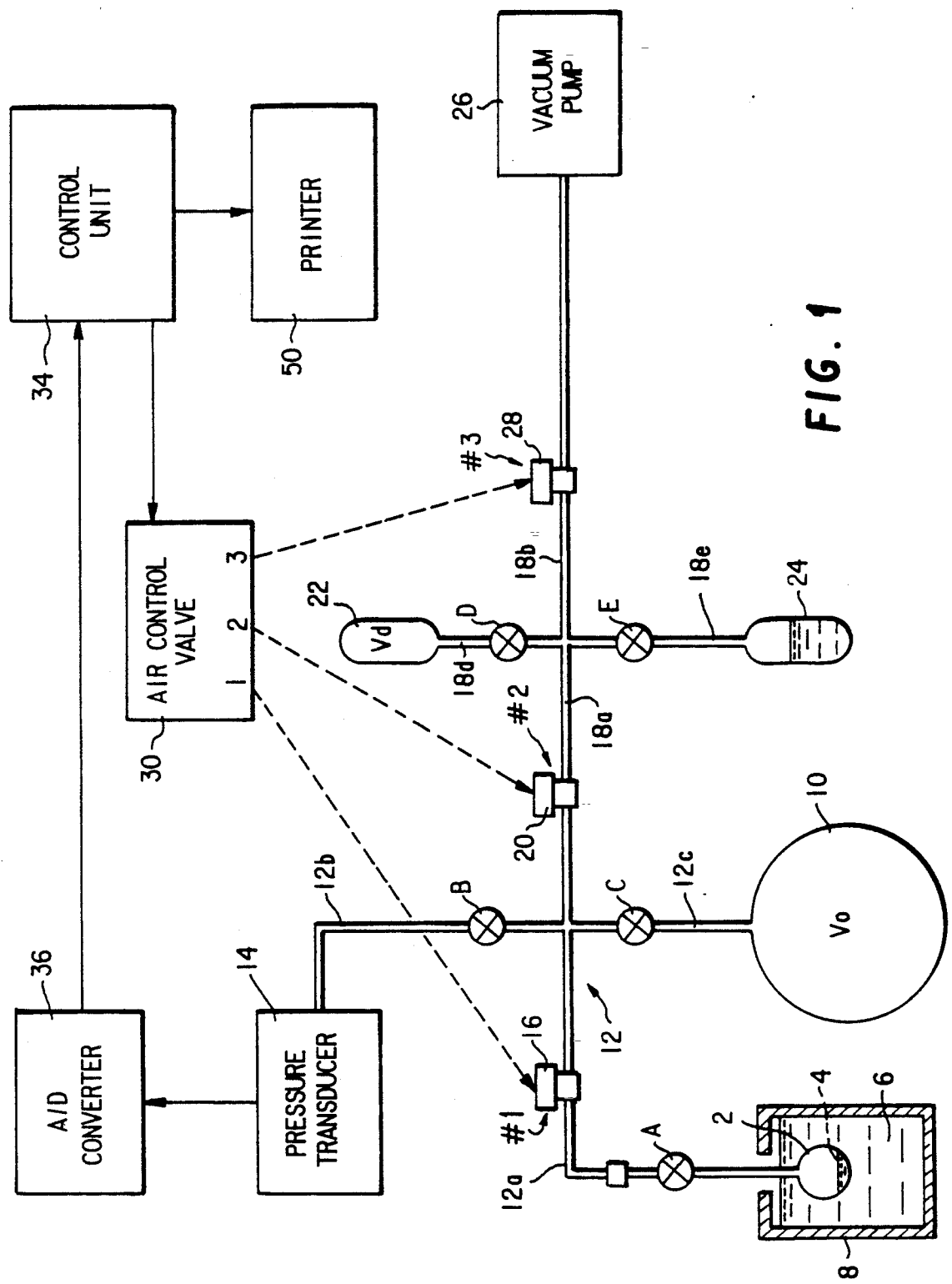
FIG. 1 is a schematic illustration of the apparatus according to the invention.

As seen in FIG. 1, the system according to the invention includes a sample holding volume in the form of a flask 2 within which may be held a sample 4 whose characteristics are to be tested. The sample flask 2 is maintained at a fixed temperature by being immersed in a liquid bath 6 within an insulated container 8.

A sealed volume takes the form of a volumetric flask 10 having a large volume relative to the sample flask 2. The volumetric flask 10 is fluidically connected to the sample flask 2 in a fluid tight manner via first conduit 12. The first conduit 12 includes a first segment 12a connected to the sample flask 2, a second segment 12c connected between the first segment and the volumetric flask 10. A third segment 12b of the first conduit connects to a pressure transducer 14 having a sensitivity of at least 0.01 Torr. The pressure transducer can be model no. 390H, manufactured by MKS Instruments, Inc. Stopcocks A, B and C are positioned within first conduit segments 12a, 12b and 12c, respectively. In addition, a first air actuated valve 16 (first valve means) is positioned in first conduit segment 12a.

A second fluid tight conduit 18 includes a first segment 18a which connects to the first conduit 12 via a second air valve 20 (second valve means) which can be actuated to provide fluid communication between first and second conduit segments 12a and 18a, respectively. The second conduit 18 also includes a segment 18d having stopcock D and connected to an evacuatable volume 22. The segment 18e of the second conduit 18 contains stopcock E and connects to a liquid holding volume in the form of a water holding flask 24 which holds a volume of water. The segment 18b of the second conduit 18 connects to a vacuum pump 26 via a third air actuatable valve 28 (third valve means).

Figure 2:
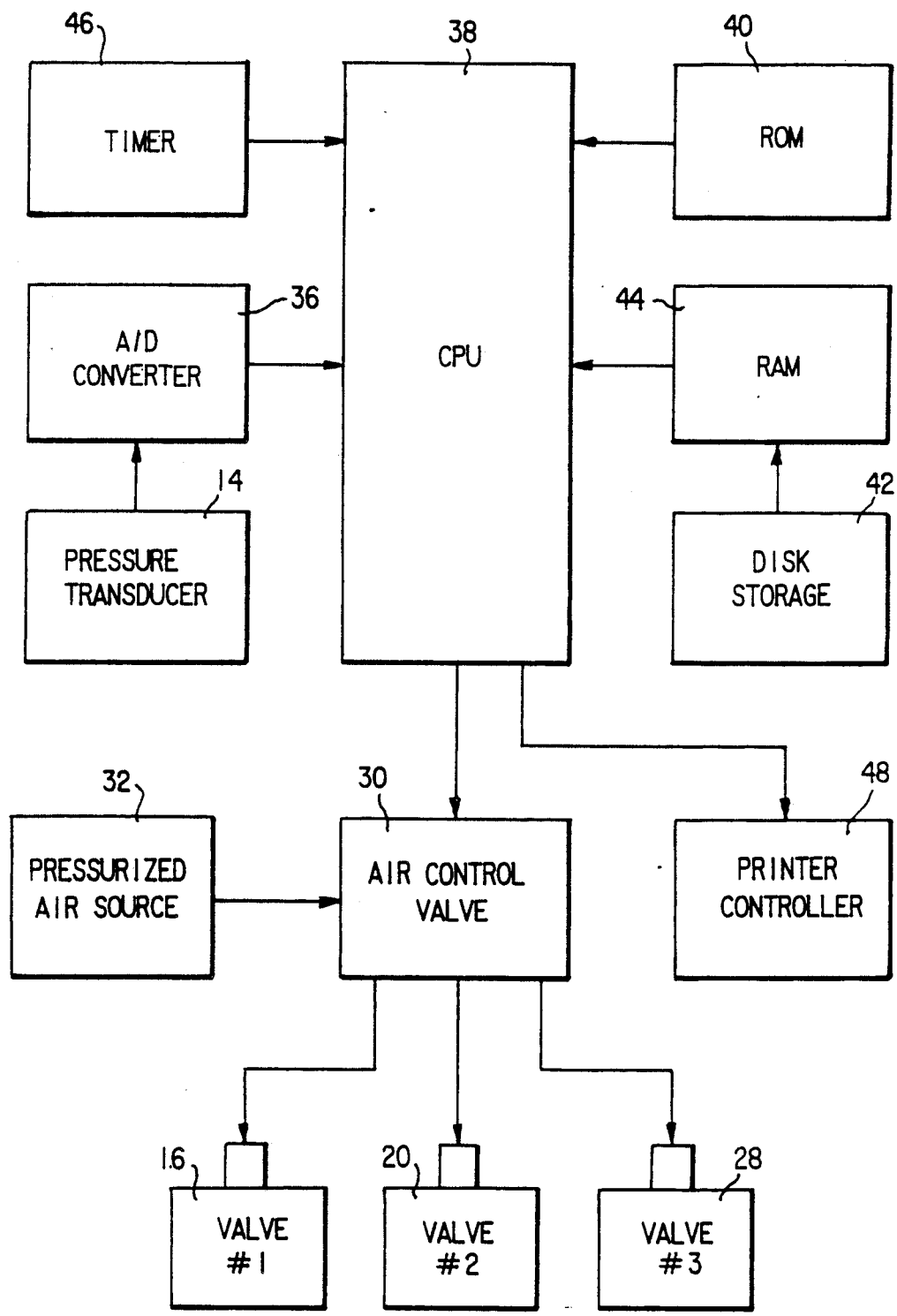
FIG. 2 is a schematic illustration of the control unit.

The air actuatable valves 16, 20 and 28 can take the form of bellows valves connected by stainless steel tubing to a conventional air control valve 30 for regulating compressed air from a compressed air source 32 (FIG. 2).

A control unit 34 receives pressure signals from the pressure transducer 14 via an analog to digital (A/D) converter 36. As best seen in FIG. 2, the control unit includes a CPU 38 which is responsive to a program stored either in ROM 40 or in a disk storage unit 42 via RAM 44. A timer 46 connects to the CPU for providing timing signals, as set forth below. The CPU in turn controls the air control valve 30 in accordance with the stored program and signals received from the timer 46 and pressure transducer 14, and also controls a printer controller 48 to operate the printer 50, as described below.

Figure 3:
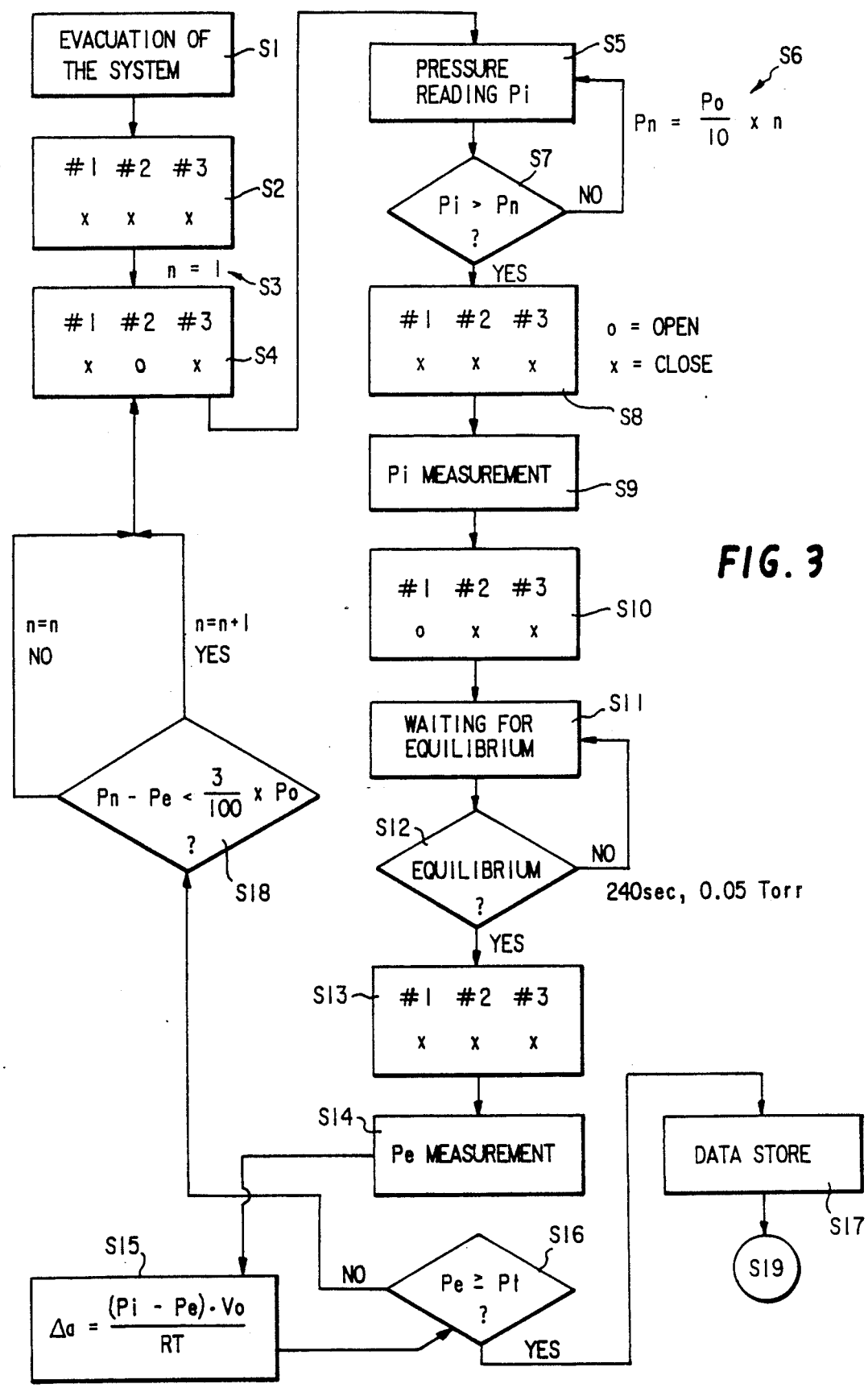
FIG. 3 is a flow chart showing the adsorption measuring means of the control unit.
Figure 4:
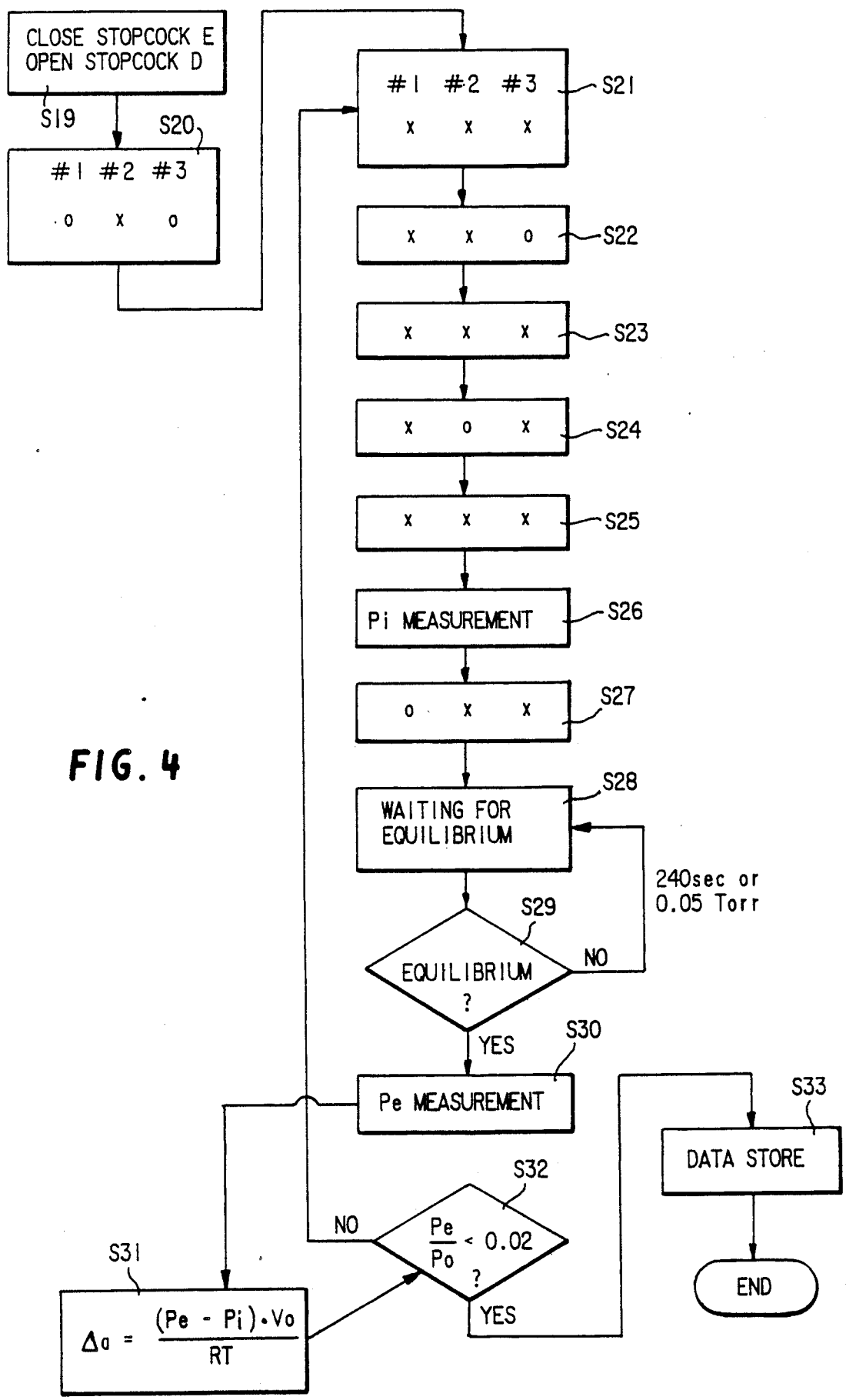
FIG. 4 is a flow chart showing the desorption measuring means of the control unit.

The program stored in the control unit comprises adsorption and desorption measuring means respectively set forth in FIGS. 3 and 4. Before starting the measurement, water in the flask 24 must be degassed so that no dissolved gases remain in the water. After degassing, the stopcock E is closed. Referring to FIG. 3 which illustrates the adsorption measuring means, once a sample has been prepared and placed in the sample flask 2, the system is evacuated in step S1 which constitutes means for simultaneously opening the first, second and third valves so that the sample flask 2, the volumetric flask 10, the evacuatable volume 22 and the water holding flask 24 are all evacuated. In step S1, the A, B, C and D stopcocks are opened while E is closed. Subsequently, in step S2, the valves 16, 20 and 28 are all closed. The stopcock D is also closed. The value n is then set to 1 in step S3.

Step S4 comprises means for opening the second valve means while the evacuatable volume is isolated from the second conduit means. For this purpose, valve 20 is opened in step 4, while valves 16 and 28 remain closed, so that water vapor in the flask 24 is permitted to enter the volumetric flask 10. The stopcock E is manually opened prior to beginning step S4.

After step S4, control moves to the means for closing the second valve means when a detected pressure in the sealed volume exceeds a predetermined fraction of a maximum tested vapor pressure. This means consists of steps S5 through S7. Step S5 comprises using the pressure transducer 14 to read the pressure $P_i$ within the system, after which control passes to step S6 which tests whether the pressure in the system exceeds a pressure $P_n$. Pressure $P_n$ corresponds to a fraction of the maximum test pressure $P_0$, and is determined by dividing the product of $P_0$ and n by the total number of test data points. For example, if adsorption is to be measured at 10 data points including $P_0$, then $P_n$ equals $P_0$ divided by 10, times n. $P_n$ is calculated in step S6. If $P_i$ is not greater than $P_n$, control is returned to step S5. If $P_i$ is greater than $P_n$, control moves to step S8 in which valves 16, 20 and 28 are all closed.

The volumetric flask 10 is now at a test pressure $P_i$ which is substantially equal to $P_n$ and the system is ready to begin the adsorption sequence. The exact value of $P_i$ for n equals 1 is first measured by the pressure transducer 14 in step S9. Control then passes to step S10 which comprises the means for subsequently opening the first valve means whereby a sample in the sample holding volume is exposed to the pressure $P_i$ and water vapor is adsorbed onto the sample.

Control then passes to the means for determining when an equilibrium pressure is detected in the sample holding means. In step S11 the CPU waits for a predetermined time, for example 240 seconds as input by the timer 46. After the predetermined time, control passes to step S12 in which it is tested whether the detected pressure has decreased by a set value, for example 0.05 Torr. If the pressure has decreased by more than the set value during the predetermined time, then it is determined in step S12 that equilibrium conditions have not yet been met and control is returned to step S11. On the other hand, if the detected pressure value has changed by less than the set value during the predetermined time, it is determined in step S12 that equilibrium conditions exist and control is passed to step S13 which constitutes means for closing the first valve means when an equilibrium pressure $P_e$ is detected in the sealed volume. This equilibrium pressure $P_e$ is then measured in step S14.

Control then passes to step S15 which is the means for determining an amount $\Delta a$ of the liquid vapor adsorbed by the sample 4. Amount $\Delta a$ is determined in step S15 according to the equation:

$$\Delta a = \frac{(P_i - P_e)V_o}{RT} \quad (1)$$

Since $P_i - P_e$ is the pressure drop during adsorption, equation 1 reduces to:

$$\Delta a = \frac{\Delta P \cdot V_o}{RT} \quad (2)$$

which is the standard gas equation, in which:

$\Delta P = P_i - P_e$, $V_0$ is the total volume of the system which includes the sample flask, the volumetric flask and the first conduit, but excluding the sample volume, R is the gas constant, and T is the absolute temperature of the vapor.

Control then advances to step S16 which comprises means for testing whether $P_e$ is larger than $P_t$ where $P_t$ is a preset pressure. $P_t$ can be equal to or smaller than $P_o$. If so, adsorption measurement up to the maximum test pressure $P_o$ has been completed and the data, including the values of $\Delta a$ at the various pressures $P_n$ is stored in step S17 in preparation for plotting.

If $P_e$ is less than $P_t$, control advances to step S18. In step S18, if the amount of adsorption $\Delta a$ is so large that the pressure difference $(P_n - P_e)$ is larger than 3% of $P_o$, i.e., the equilibrium pressure $P_e$ is far below the predetermined fraction pressure $P_n$, the same $P_n$ is used for the next adsorption step and control is returned to step S4 without raising the value of n. If $P_n - P_e$ is smaller than 3% of Po, n is raised to n+1, and a higher fraction pressure $P_n + 1$ is used in step S4. The cycle continues until $P_e$ is determined to be larger than or equal to $P_t$ at step S16.

The means for measuring desorption of water vapor from the sample is substantially similar to the adsorption measuring means of FIG. 3, and is shown in FIG. 4. Once the adsorption data is stored in step S17, control passes to the desorption cycle and the stopcock D is opened while the stopcock E is closed in step S19. In step S20, the valves 16 and 28 are opened while the valve 20 is closed, so that water vapor is evacuated from the second conduit 18 and the volumetric flask 10 is at the same pressure $P_i$ as the sample flask 2.

After all of the valves are closed in step S21, valve 28 is opened and closed so that the second conduit 18 may be evacuated in subsequent cycles (control is returned to step S21 after testing at each pressure data point). This opening and closing of valve 28 is shown at steps S22 and S23.

Step S24 comprises the means for opening the second valve means 20 so that the pressure $P_i$, which is initially approximately equal to $P_t$, communicates with the evacuatable volume and so has its value reduced. In step S25 all of the valves are again closed and the exact value of $P_i$ is then measured at step S26.

Step S27 constitutes the means for subsequently opening the first valve means so that the sample in the sample holding volume is exposed to the pressure $P_i$ and liquid vapor is desorbed from the sample 4.

Equilibrium is then tested for in steps S28 and S29 in a manner similar to that in the adsorption cycle. Once equilibrium is reached, the equilibrium pressure $P_e$ is measured in step S30.

Step S31 determines the value of $\Delta a$ according to equation 2, with the exception that $\Delta P$ equals $P_e - P_i$.

In step S32 it is determined whether all of the data pressure points have been sampled by testing whether the ratio $P_e/P_o$ is less than a predetermined value, for example 0.02. If so, data is stored for plotting at step S33, otherwise control returns to step S21.

As a result of the above process and structure, there will be stored data corresponding to $\Delta a$ at various equilibrium vapor pressures $P_e$. This data can be used for producing isotherm plots, BET plots and Langmuir plots which may be printed by the printer 50 under the control of the CPU 38 and the printer controller 48.

EXAMPLE 1

Figure 5A:
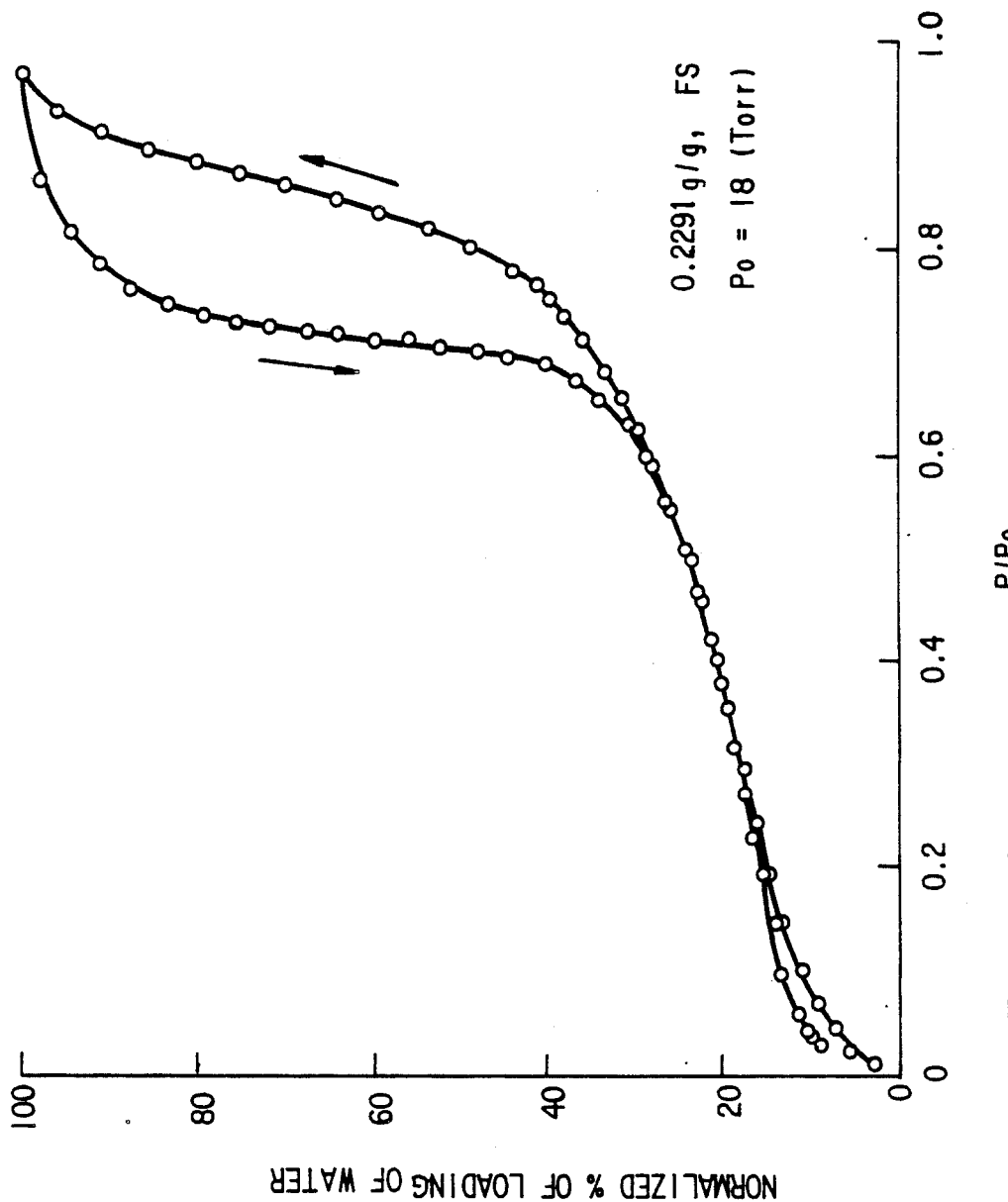
FIG. 5A is an isotherm plot of adsorption and desorption characteristics of a sample according to a first example.

Vycor porous glass was heated at 300° C. and found to weigh 91.0 mg, after which it was degassed at 200° C. in a vacuum. The glass sample was then placed in a sample flask 2 and its temperature was stabilized at 20° C. Water vapor adsorption characteristics of the sample were then tested at various pressures up to a pressure $P_0 = 18$ Torr. The total water vapor adsorption porosity was found to be 0.2291 grams per gram, according to the isotherm plot of FIG. 5A. The desorption isotherm shows a hysteresis due to an ink-bottle structure in the interconnected pores.

Figure 5B:
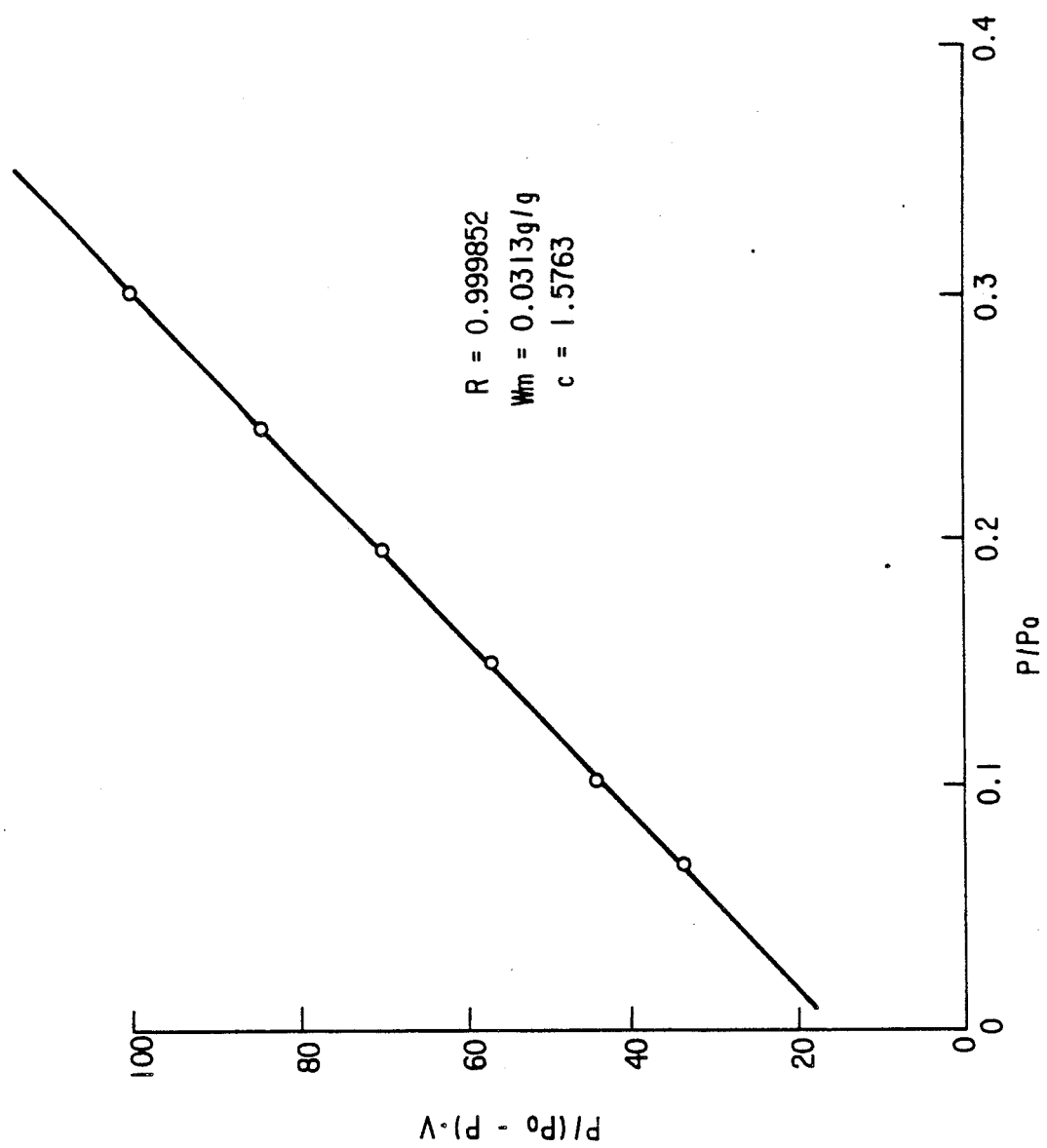
FIG. 5B corresponds to FIG. 5A, but shows a BET plot.
Figure 5C:
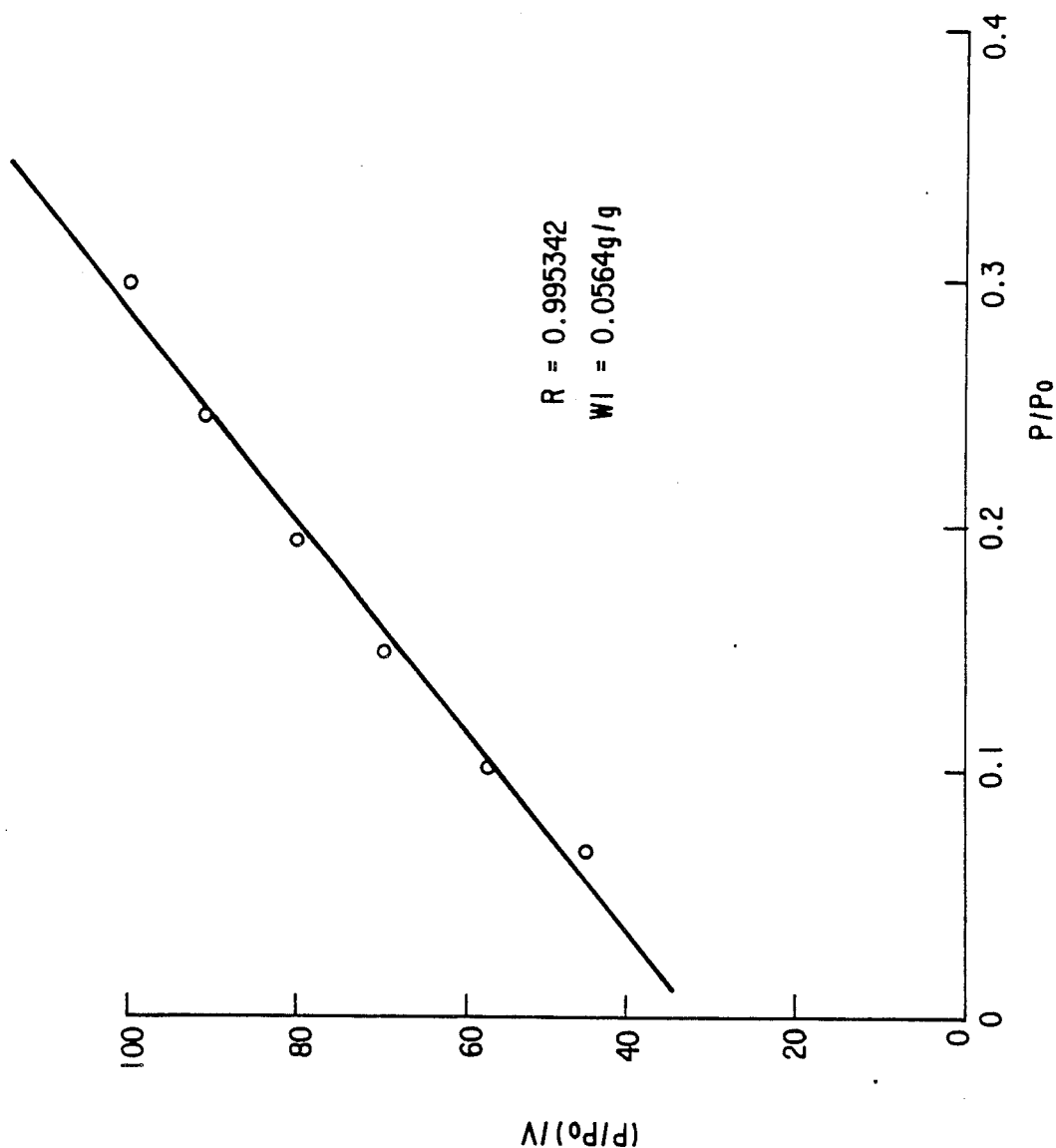
FIG. 5C corresponds to FIG. 5A, but shows a Langmuir plot.

The BET plot for the same sample is shown in FIG. 5B, while the C. C. Langmuir plot for the same sample is shown in FIG. 5C.

EXAMPLE 2

Figure 6A:
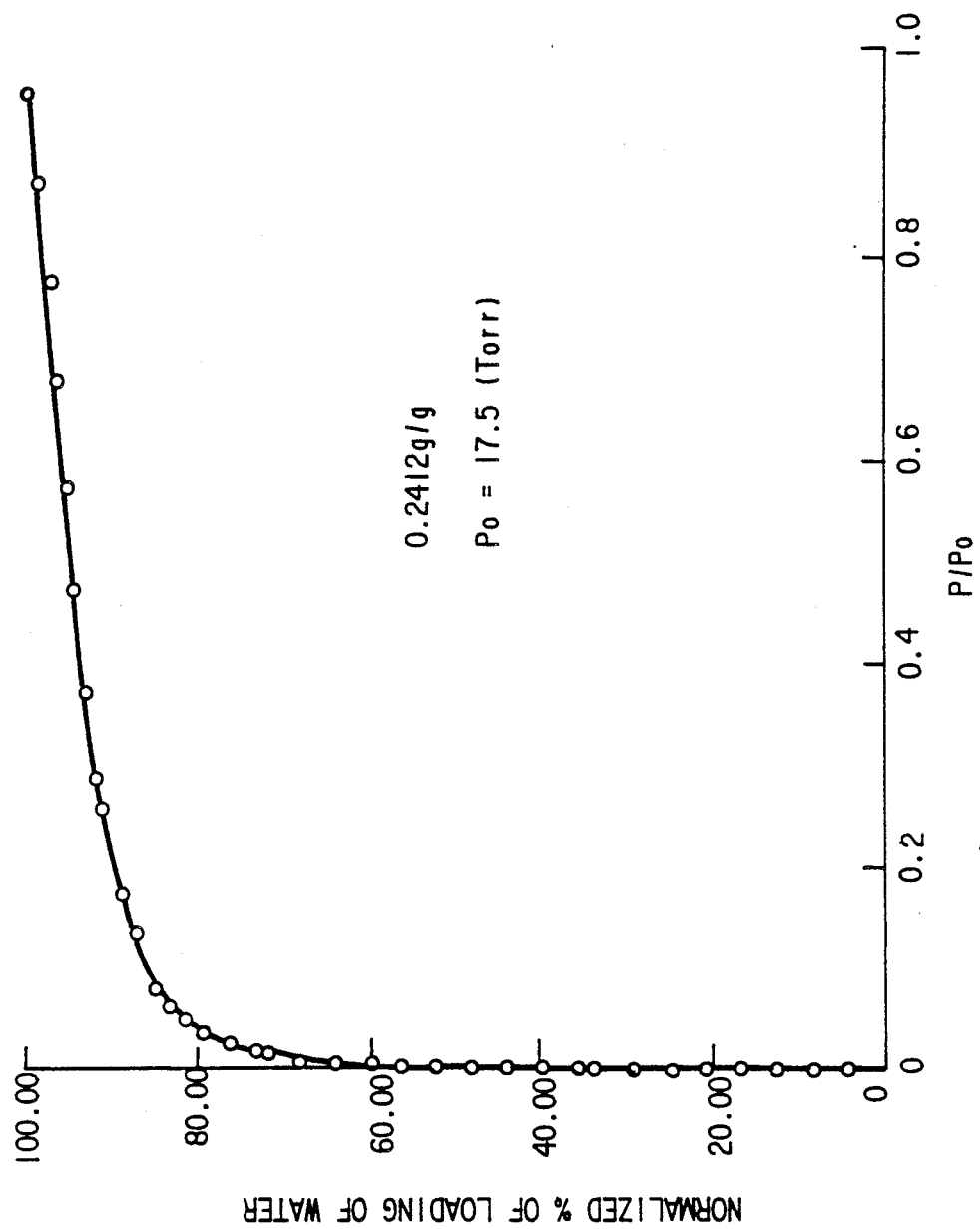
FIG. 6A corresponds to FIG. 5A, but is for a second example.
Figure 6B:
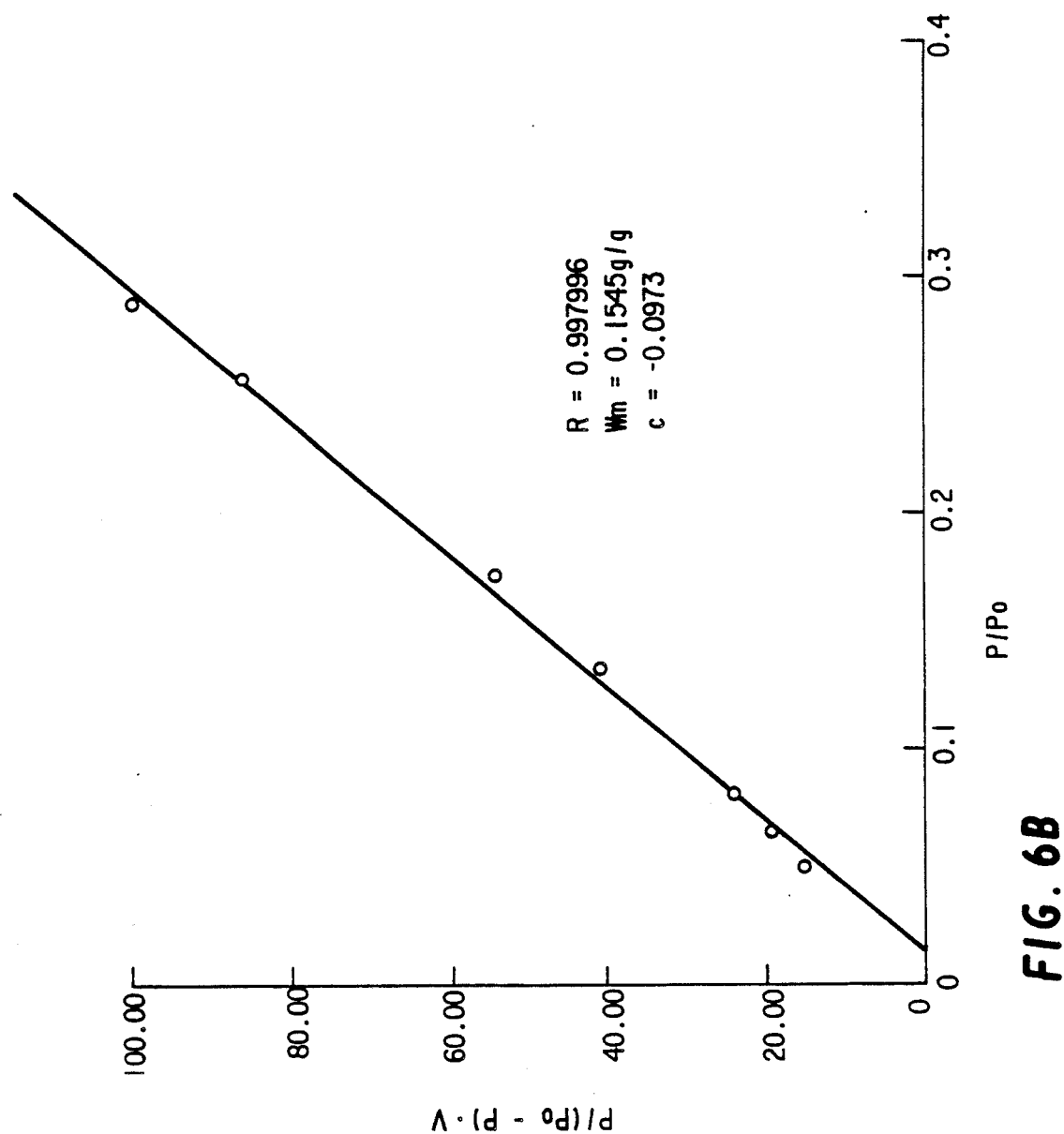
FIG. 6B corresponds to FIG. 5B, but is for a second example.
Figure 6C:
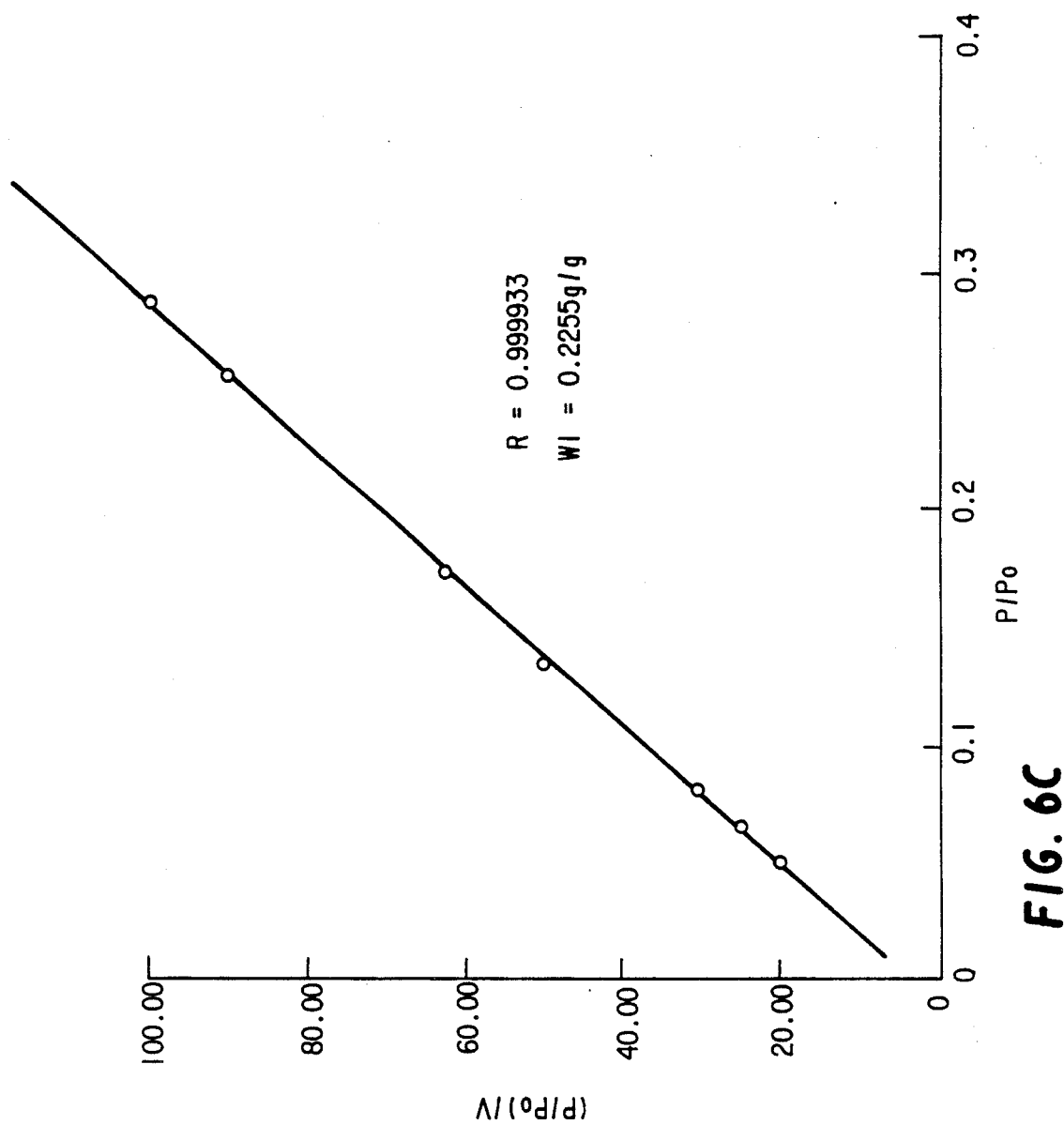
FIG. 6C corresponds to FIG. 5C, but is for a second example.

A zeolite 4A sample was sieved to −200 mesh and heated at 400° C. in air, after which it was weighed at 108.6 mg. After degassing at 200° C. in a vacuum, its adsorption/desorption characteristics were sampled according to the invention up to 18 Torr, from which the isotherm plot of FIG. 6A was produced. The corresponding BET and Langmuir plots are shown in FIGS. 6B and 6C. The adsorption capacity of the sample was determined to be 0.2412 ml/g.

Obviously, numerous modifications and variations of the present invention are possible in light of the above teachings. It is therefore to be understood that within the scope of the appended claims, the invention may be practiced otherwise than as specifically described herein.

What is new and desired to be secured by Letters Patent of the United States is:

1. An apparatus for measuring liquid vapor adsorption and desorption characteristics of a sample, comprising:

a fluid tight sample holding volume;

a sealed volume;

pressure sensing means;

first fluid tight conduit means for fluidically communicating said sample holding volume, said sealed volume and said pressure sensing means;

a liquid holding volume;

an evacuatable volume;

second fluid tight conduit means for fluidically communicating said liquid holding volume and said evacuatable volume;

vacuum forming means;

first automatically controllable valve means in said first conduit means, selectively actuatable for isolating said sample holding volume from said sealed volume and said pressure sensing means;

second automatically controllable valve means, selectively actuatable for fluidically communicating said first and second conduit means;

means for selectively isolating at least one of said liquid holding volume and said evacuatable volume from said second conduit means;

third automatically controllable valve means selectively actuatable for fluidically communicating said vacuum forming means with said second conduit means; and control means including:
(a) means for receiving pressure signals from said pressure sensing means,
(b) means for storing a program, and
(c) means responsive to said pressure signals for selectively controlling said first, second and third valve means in accordance with a program stored in said program storing means.

2. The apparatus of claim, 1 wherein said means for selectively controlling said first, second and third valve means includes means:

for simultaneously opening said first, second and third valve means, whereby said sample holding volume, said sealed volume, said liquid holding volume and said evacuatable volume are evacuated;

for subsequently opening said second valve means while said evacuatable volume is isolated from said second conduit means, whereby liquid vapor in said liquid holding volume is permitted to enter said sealed volume;

for closing said second valve means when a detected pressure $P_i$ in said sealed volume exceeds a predetermined fraction $P_n$ of a maximum tested vapor pressure $P_o$;

for subsequently opening said first valve means, whereby a sample in said sample holding volume is exposed to said pressure $P_i$ and liquid vapor is adsorbed on said sample; and for closing said first valve means when an equilibrium pressure $P_e$ is detected in said sealed volume.

3. The apparatus of claim 2 wherein said control means including means for determining an amount $\Delta a$ of liquid vapor adsorbed by the sample, based upon a value of $P_i - P_e$.

4. The apparatus of claim 3 wherein said control means further comprises means for testing whether $P_e \geq P_t$, where $P_t$ is a preset pressure equal to or smaller than $P_o$.

5. The apparatus of claim 4 wherein said control means includes means for testing whether $\Delta a$ is greater than a threshold value and increasing $P_n$ to a larger fraction of $P_o$ when $\Delta a$ is not less than the threshold value and $P_e < P_t$.

6. The apparatus of claim 5 wherein said means for selectively controlling said first, second and third valve means further comprise means:

for opening said second valve means when $P_i \sim P_t$ and said liquid holding volume is isolated from said second conduit means, whereby liquid vapor in said sealed volume is evacuated to said evacuatable volume;

for subsequently closing said second valve means;

for subsequently opening said first valve means, whereby the sample in said sample holding volume is exposed to said pressure $P_i$ and liquid vapor is desorbed from said sample; and for closing said first valve means when an equilibrium pressure $P_e$ is detected in said sample holding means.

7. The apparatus of claim 6 wherein said control means further includes means for determining the amount $\Delta a$ desorbed by the sample based on the value of $P_e - P_i$.

8. The apparatus of claim 7 wherein control means further comprises means for testing whether $$\frac{P_e}{P_o}$$

is less than a predetermined value and storing value of $\Delta a$ when $$\frac{P_e}{P_o}$$

is less than said predetermined value.

9. The apparatus of claim 2 wherein said control means comprise a digital computer.

10. The apparatus of claim 2 wherein said first, second and third valve means comprise air actuated valves.

11. The apparatus of claim 2 wherein said control means include means for determining when an equilibrium pressure is detected in said sample holding means, comprising:

timer means for detecting the passage of a predetermined time; and means for outputting an equilibrium pressure signal when $P_i$ changes by less than a set value during said predetermined time.

12. The apparatus of claim 2 including means for plotting values of $\Delta a$ at different values of $P_e$.

13. The apparatus of claim 1 wherein said pressure sensing means comprises a pressure senor having a sensitivity of 0.01 Torr.

* * * * *